United States Patent
Zhang et al.

(10) Patent No.: US 9,314,590 B2
(45) Date of Patent: Apr. 19, 2016

(54) METHOD AND APPARATUS FOR RETROPERFUSION

(75) Inventors: Li Zhang, Winnipeg (CA); Farrukh Hussain, Winnipeg (CA)

(73) Assignee: University of Manitoba, Winnipeg, Manitoba (CA)

( * ) Notice: Subject to any disclaimer, the term of this patent is extended or adjusted under 35 U.S.C. 154(b) by 336 days.

(21) Appl. No.: 13/704,525

(22) PCT Filed: Jun. 14, 2011

(86) PCT No.: PCT/CA2011/000704
§ 371 (c)(1),
(2), (4) Date: Jul. 19, 2013

(87) PCT Pub. No.: WO2011/156904
PCT Pub. Date: Dec. 22, 2011

(65) Prior Publication Data
US 2013/0296783 A1    Nov. 7, 2013

Related U.S. Application Data

(60) Provisional application No. 61/354,616, filed on Jun. 14, 2010.

(51) Int. Cl.
*A61M 1/36* (2006.01)
*A61M 1/10* (2006.01)
*A61M 25/00* (2006.01)
(Continued)

(52) U.S. Cl.
CPC .......... *A61M 25/0075* (2013.01); *A61M 1/3613* (2014.02); *A61M 5/16881* (2013.01); *A61M 25/0074* (2013.01); *A61M 39/227* (2013.01); *A61M 39/228* (2013.01); *A61M 1/36* (2013.01);
(Continued)

(58) Field of Classification Search
CPC ............ A61M 2025/1072; A61M 2025/0079; A61M 2025/1045; A61M 2025/1059; A61M 2005/1406; A61M 5/16813; A61M 2039/2413; A61M 1/1018; A61M 39/227; A61M 39/228; A61M 25/0074; A61M 25/0075; A61M 2025/0076; A61M 2025/0078; A61M 5/16881; A61M 2039/2433; A61M 1/3613; A61M 39/28
See application file for complete search history.

(56) References Cited

U.S. PATENT DOCUMENTS 3,717,174 A * 2/1973 Dewall .................... A61M 5/36
137/565.15
3,759,289 A * 9/1973 DeWall .................... A61M 5/36
137/844

(Continued)

*Primary Examiner* — Emily Schmidt
*Assistant Examiner* — William Frehe
(74) *Attorney, Agent, or Firm* — Gowling WLG (Canada) LLP

(57) ABSTRACT

The present invention relates to apparatus for retroperfusion of tissues and organs. The apparatus comprises a catheter with a proximal end for engaging a supply of the fluid medium, and a distal end having an expandable-contractible chamber for installation into suitable vessels or organs. The expandable-contractible chamber comprises a conduit element having a fluid-filled hollow wall defining a lumen. The conduit element has a first deformable inner-facing section approximate a proximal end of the conduit and a second deformable inner-facing section approximate a distal end of the conduit element. Controlled application of a pressure at a proximal end of the conduit element causes deformation of the conduit into the lumen at its distal end thereby occluding the flow of fluid medium through the catheter. Controlled release of the pressure releases deformation of the fluid-filled conduit at its distal end thereby unblocking the flow of the fluid medium through the catheter.

15 Claims, 4 Drawing Sheets

(51) Int. Cl.
*A61F 2/958* (2013.01)
*A61M 39/22* (2006.01)
*A61M 5/168* (2006.01)
*A61M 25/10* (2013.01)

(52) U.S. Cl.
CPC ........ *A61M 25/10* (2013.01); *A61M 2025/1059* (2013.01); *A61M 2025/1072* (2013.01)

(56) References Cited

U.S. PATENT DOCUMENTS

| | | | | |
|---|---|---|---|---|
| 4,227,533 A * | 10/1980 | Godfrey | ............ | A61M 25/0075 604/247 |
| 4,722,725 A * | 2/1988 | Sawyer | ................... | A61M 5/36 604/122 |
| 5,112,301 A * | 5/1992 | Fenton, Jr. | ............ | A61M 1/008 604/247 |
| 5,360,403 A * | 11/1994 | Mische | ............ | A61M 25/0075 604/101.02 |
| 5,441,485 A * | 8/1995 | Peters | ............... | A61M 25/1002 604/101.01 |
| 5,533,957 A * | 7/1996 | Aldea | .................... | A61M 1/36 128/898 |
| 5,904,701 A * | 5/1999 | Daneshvar | ............. | A61B 17/24 128/DIG. 25 |
| 6,138,984 A * | 10/2000 | Abell | .................. | A61M 3/0258 251/4 |
| 7,833,186 B1 * | 11/2010 | Batiste | ................ | A61M 1/3655 604/509 |
| 2004/0044307 A1 * | 3/2004 | Richardson | ........... | A61F 2/0013 604/102.01 |
| 2004/0054348 A1 * | 3/2004 | Hogendijk | ........ | A61M 5/16813 604/523 |
| 2005/0131344 A1 * | 6/2005 | Godaire | ........... | A61M 25/0075 604/99.04 |
| 2007/0093749 A1 * | 4/2007 | Spranger | ............... | A61M 1/367 604/99.01 |
| 2009/0118681 A1 * | 5/2009 | Molgaard-Nielsen | | A61M 39/0613 604/246 |
| 2009/0221992 A1 * | 9/2009 | Hannon | ............ | A61M 25/0017 604/544 |
| 2009/0270815 A1 * | 10/2009 | Stamp | ................ | A61M 25/0075 604/249 |
| 2009/0302244 A1 * | 12/2009 | Wedel | ................ | A61M 39/284 251/5 |

* cited by examiner

METHOD AND APPARATUS FOR RETROPERFUSION

TECHNICAL FIELD

The present invention relates to apparatus and methods for retroperfusion of myocardium. More specifically, the present invention relates to apparatus for retroperfusion of myocardium with a patient's arterial blood supply.

BACKGROUND

Ischemic myocardium is vulnerable if revascularization cannot be achieved immediately. When one or more of the coronary arteries are blocked or otherwise unable to convey oxygenated blood to the heart muscles, tissue damage can occur in minutes.

Retroperfusion refers to a process where oxygenated blood is sent through the veins to irrigate and oxygenate the tissue in a direction opposite to normal blood flow. Coronary sinus retroperfusion techniques have been demonstrated to delay and/or reverse ischemic changes in the myocardial tissue, and may decrease infarct size and improve ventricular function following an infarction.

Pressure-controlled intermittent coronary sinus retroperfusion (PICSO) involves placing a device to periodically occlude the coronary sinus. When the device is inflated, venous blood draining into the coronary sinus is retained and passively redirected within the coronary venous system. While the mechanism is relatively simple, perfusing the myocardium with oxygen depleted venous blood may be less effective (additional oxygen is not being introduced to the tissue, and may also cause accumulation of toxic metabolites in the myocardium).

Synchronized retroperfusion (SRP) involves placement of a conduit catheter into the coronary sinus, and in synchrony with conduit inflation, oxygenated blood is pumped into the coronary venous system in a retrograde manner. Conduit inflation and blood injection into the coronary sinus occurs during diastole. The conduit is deflated during systole and blood flow into the coronary sinus ceases. SRP may involve use of complex pressure monitoring devices and pumps, and may require substantive setup, thus consuming precious time when re-establishing revascularization of the myocardium.

Simplified retroperfusion (SR) is similar to SRP, but does not include occlusion of the coronary sinus. Oxygenated blood is continuously injected into the coronary sinus with an infusion pump. While the tissue may be oxygenated, backflow into the right atrium instead of the coronary venous system may occur.

SUMMARY OF THE INVENTION

The exemplary embodiments of the present invention relate to apparatus and methods for retroperfusion of myocardium. More specifically, the present invention relates to a catheter for retroperfusion of myocardium with a patient's own arterial blood flow. Retroperfusion of the myocardium may be performed prior to, during, or following an interventional procedure (e.g. angioplasty, coronary artery bypass graft, heart transplant, any open-heart surgery, and the like).

According to an exemplary embodiment of the present invention, the apparatus comprises a catheter configured for insertion into a coronary sinus and controllable selective occlusion of the coronary sinus. The catheter is configured for conveying a supply of oxygenated blood from an arterial supply source to the coronary sinus of the heart. The catheter comprises a conduit connectable about its proximal end to the supply source of oxygenated blood, and a chamber about the distal end of the catheter. A sealed, fluid-filled manually decompressable conduit is disposed within the chamber. The proximal end of the sealed, fluid-filled conduit is provided with a pocket area that deforms inward when pressurized, e.g., by a flow of fluid medium thereagainst. When the pocket is pressurized with oxygenated blood during systole and in synchrony with the cardiac cycle, the increased pressure on the fluid sealed within the conduit deforms a first diaphragm within the conduit causing the fluid of the sealed, fluid-filled conduit to be displaced towards a second diaphragm, which is in turn displaced to occlude the first lumen of the catheter thereby preventing the flow of the oxygenated blood within the lumen. As pressure in the pocket is reduced (e.g. during diastole), pressures on the first and second diaphragms are relieved, and the fluid-filled conduit retracts from occluding the first lumen, and retrograde flow of the oxygenated blood within the coronary sinus may occur.

BRIEF DESCRIPTION OF THE DRAWINGS

These and other features of the invention will become more apparent from the following description in which reference is made to the appended drawings wherein.

DETAILED DESCRIPTION

Unless otherwise defined, all technical and scientific terms used herein have the same meaning as commonly understood by one of ordinary skill in the art to which this invention belongs. In order that the invention herein described may be fully understood, the following terms and definitions are provided herein.

The word "comprise" or variations such as "comprises" or "comprising" will be understood to imply the inclusion of a stated integer or groups of integers but not the exclusion of any other integer or group of integers.

The term "about" or "approximately" means within 20%, preferably within 10%, and more preferably within 5% of a given value or range.

The term "coronary sinus" refers to a collection of veins joined together to form a single vein that collects blood from the myocardium of the heart. The coronary sinus delivers oxygen-depleted blood from the myocardium to the right atrium of the heart interposed the superior vena cava and the inferior vena cava.

The term "myocardium" refers to the cardiac muscle which is comprised of myocardiocyteal muscle cells. The cardiac muscles cells contract in a coordinated fashion expel to blood out of the atria and ventricles to arterial blood vessels.

The term "systole" refers to the period of time during which the cardiac muscle is contracting and thereby expelling blood from the ventricles.

The term "diastole" refers to the period of time during which the cardiac muscle is relaxing thereby allowing filling of the ventricles.

The term "ischemia" means a condition during supply the flow of blood to the myocardium is reduced to such low levels that that myocardium becomes oxygen-deprived. This condition results in death of myocardial cells and tissues.

The term "infarct" refers to an area of dead, i.e., necrotic myocardial cells and tissues. Myocardial infarcts are common causes of death.

The term "retroperfusion" refers to a process whereby an ischemic myocardium is perfused with oxygenated blood via the coronary venous system or with an oxygenated blood replacement product to deliver oxygen nutrition to anoxic myocardiocyteal muscle cells to reduce the size of infarcts formed during oxygen deprivation, to restore contractile activity of the myocardium, and to improve myocardial energy metabolism.

Exemplary embodiments of the present invention relate to apparatus and methods for retroperfusion of myocardium. More specifically, the present invention relates to an apparatus comprising a catheter having a chamber cooperable with an expandible-contractible conduit for controllable retroperfusion of a patient's myocardium with their own oxygenated blood.

Figure 1:
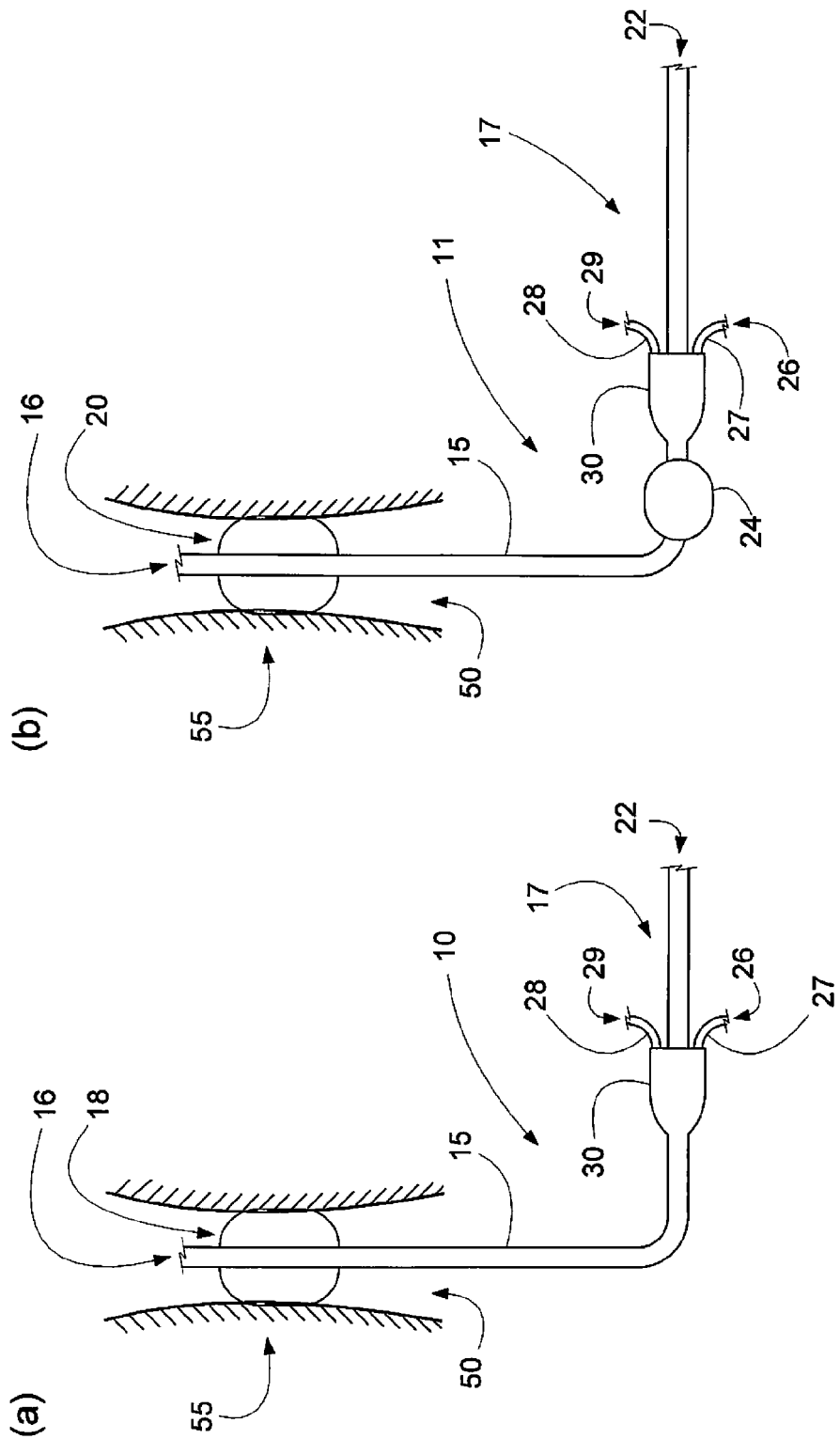
FIGS. 1(a) and 1(b) are cross-sectional views showing a first exemplary apparatus and a second exemplary apparatus of the present invention, both installed in a coronary sinus.
Figure 2:
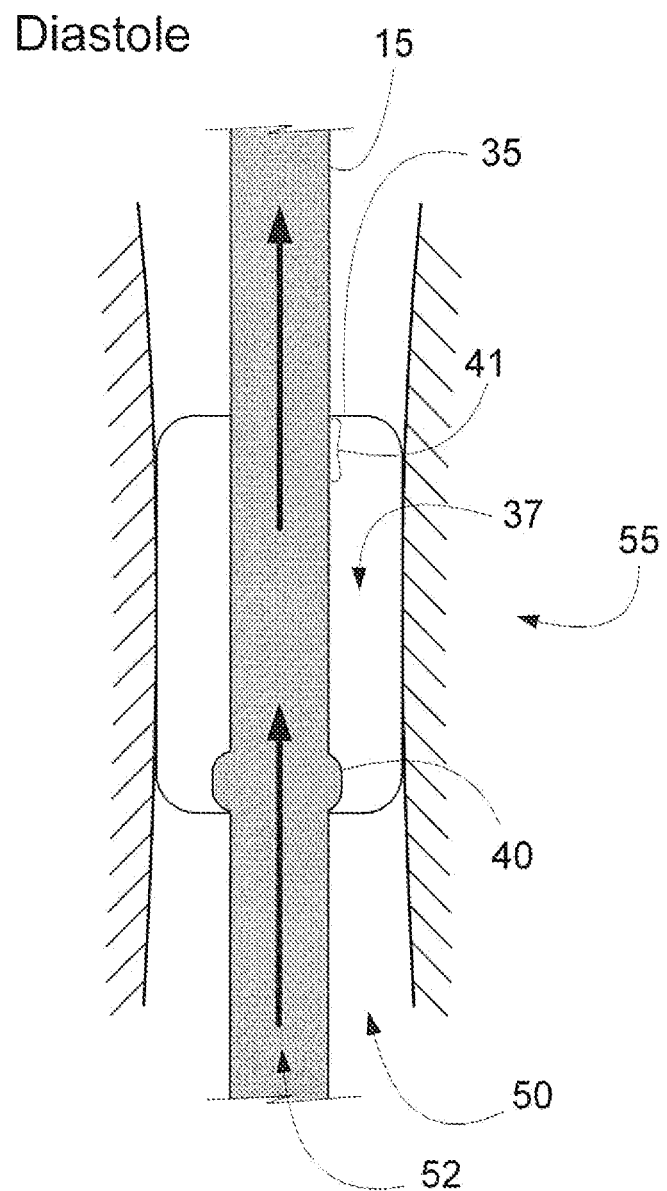
FIG. 2 is a longitudinal cross-sectional view of the installed conduit element from FIGS. 1(a) and 1(b), during diastole.
Figure 3:
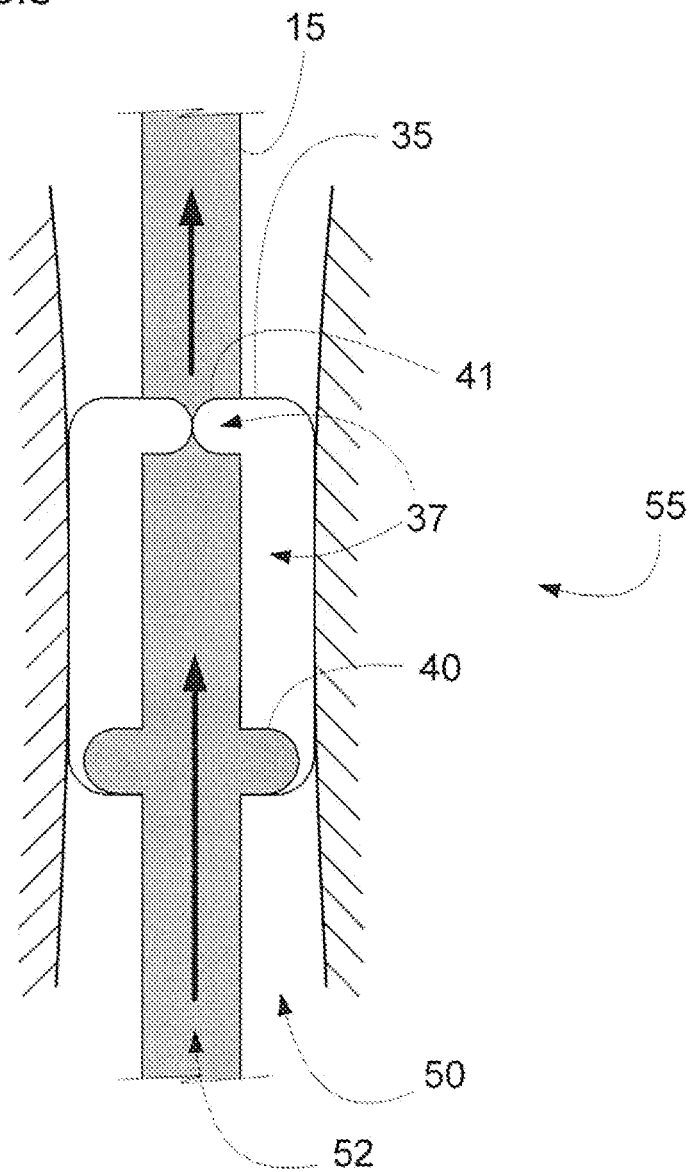
FIG. 3 is a longitudinal cross-sectional view of the installed conduit element from FIG. 2, during systole.

An exemplary apparatus according to an embodiment of the present invention is shown generally at 10 in FIG. 1(a). The apparatus comprises a catheter 15 shown with its distal end 16 inserted into the coronary sinus 50 of a heart. About the distal end 16 of the catheter is a chamber section 18 comprising a hollow-walled conduit element 35 (FIGS. 2 and 3). The chamber 37 of the hollow-walled element 35 is filled with a selected displaceable medium exemplified by fluids, gels, gases and the like, sealably contained therein. The distal end 16 of the catheter 15 is installed into a subject's coronary sinus 50 such that the chamber section 18 of the catheter 15 is in contact with an interior wall 55 of the coronary sinus 50, and prevents antegrade blood flow between the chamber section 18 and the interior wall 55 of the coronary sinus 50. The proximal end 17 of the catheter 15 is provided with an inlet 22 for engaging a conduit (not shown) supplying a flow of oxygenated blood from a suitable artery within the subject's body. Suitable arteries include the aorta, subclavian artery, brachiocephalic artery, radial artery and femoral artery. Pressure within the coronary sinus 50 and/or the catheter 15 may be monitored by a pressure monitoring device (not shown) connected to the catheter 15 by inlet 26 and tube 27. Tube 27 is sealingly engaged with the catheter 15. Tube 27 may be used as a route for manual decompression of the fluid-filled conduit inside the catheter. Optionally, a second tube 28 having a disengagably capped inlet 29 is sealingly engaged with the catheter 15 for administration of drugs or alternatively, for drawing of blood while the apparatus 10 is installed in a subject. The catheter 15 may be provided with a collar 30 to encompass and shield the juncture(s) of tubes 27 and/or 28 with the catheter 15.

An exemplary apparatus according to another exemplary embodiment of the present invention is shown generally at 11 in FIG. 1(b). In situations where the inner diameter of a patient's coronary sinus 50 is too small for installation of the chamber section 18 as shown in FIG. 1(a), a manually inflatable balloon 20 sealably connected to tube 27 is installed into the coronary sinus so that it abuts against the proximal area of the coronary sinus 50. The chamber section 18 shown in FIG. 1(a) is moved to an extracoporeal position 24 approximate the inlet 22 of the catheter 15 (FIG. 1(b)). The balloon 20 may be controllably inflated and deflated to engage and disengage the interior wall 55 of the coronary sinus 50, by a introducing or withdrawing a suitable fluid or gas from a supply engaged with the inlet 26 end of tube 27.

Referring to FIGS. 2 and 3, the proximal end of the hollow-walled conduit element 35 comprises an inner-facing area formed into a concave pocket defined by a deformable first diaphragm 40 conduit element 35. The concave pocket encircles and communicates with the lumen of the catheter 15. A resiliently deformable second diaphragm 41 is provided at the distal end of the hollow-walled conduit element 35. The second diaphragm 41 encircles and communicates the lumen of the catheter 15. The displaceable medium sealed within the chamber 37 is controllably shiftable to alternately occlude and to allow flow of oxygenated blood 52 through the catheter 15 in synchrony with a subject's cardiac cycle. During the systolic phase (FIG. 3), pressurized oxygenated blood flows (shown by the arrow 52) into the concave pocket and pushes on the first diaphragm 40 causing the first diaphragm 40 to progressively into the hollow-walled conduit element 35 thereby causing displacement of the medium toward the second diaphragm 41. The displacement of the medium within the hollow wall causes the second diaphragm 4 to deform from its resting position outward into the lumen of the catheter 15, thereby increasingly occluding the flow of oxygenated blood 52 through the catheter 15. During the diastolic phase (FIG. 2), pressurized flow of oxygenated blood 52 through the catheter 15 decreases (shown by the arrow) thus allowing oxygenated blood 52 to flow out of the concave pocket at the proximal end of the hollow-walled conduit element 35 formed during the systolic phase, thereby reducing and releasing pressure on the first diaphragm 40 allowing it to return to its resting position shown in FIG. 2. This in turn allows the displaceable medium sealed within the hollow wall of the hollow-walled conduit element 35 to reduce and release pressure on the distended second diaphragm 41 allowing it to return to its resting position resulting in removal of the occlusion of the lumen of the catheter 15 shown in FIG. 3.

Pressure within the sealed hollow-walled conduit element 35 is sufficient to deform the second diaphragm 41 to the extent where an occluded barrier to fluid flow through the catheter 15 is provided during systole. As an example, the pressure within the sealed, fluid filled conduit may be about 60 to 70 mmHg, 50 to 80 mmHg, 40 to 90 mmHg, 30 to 100 mmHg.

Occlusion of blood flow within the coronary sinus during systole affected by an exemplary apparatus of the present invention may be partial, or full. Full occlusion is occlusion of about 90% or greater of blood flow. Partial occlusion is occlusion from about 10% to about 90% blood flow, or any amount therebetween, for example, 20, 30, 40, 50, 60, 70 or 80%, or any amount therebetween. The degree of occlusion may be controllably varied by the modulating pressure applied to oxygenated blood within the catheter 15, pressure within the sealed displaceable medium-filled conduit element 19, and/or the deformation properties of the pocket area 35.

Figure 4:
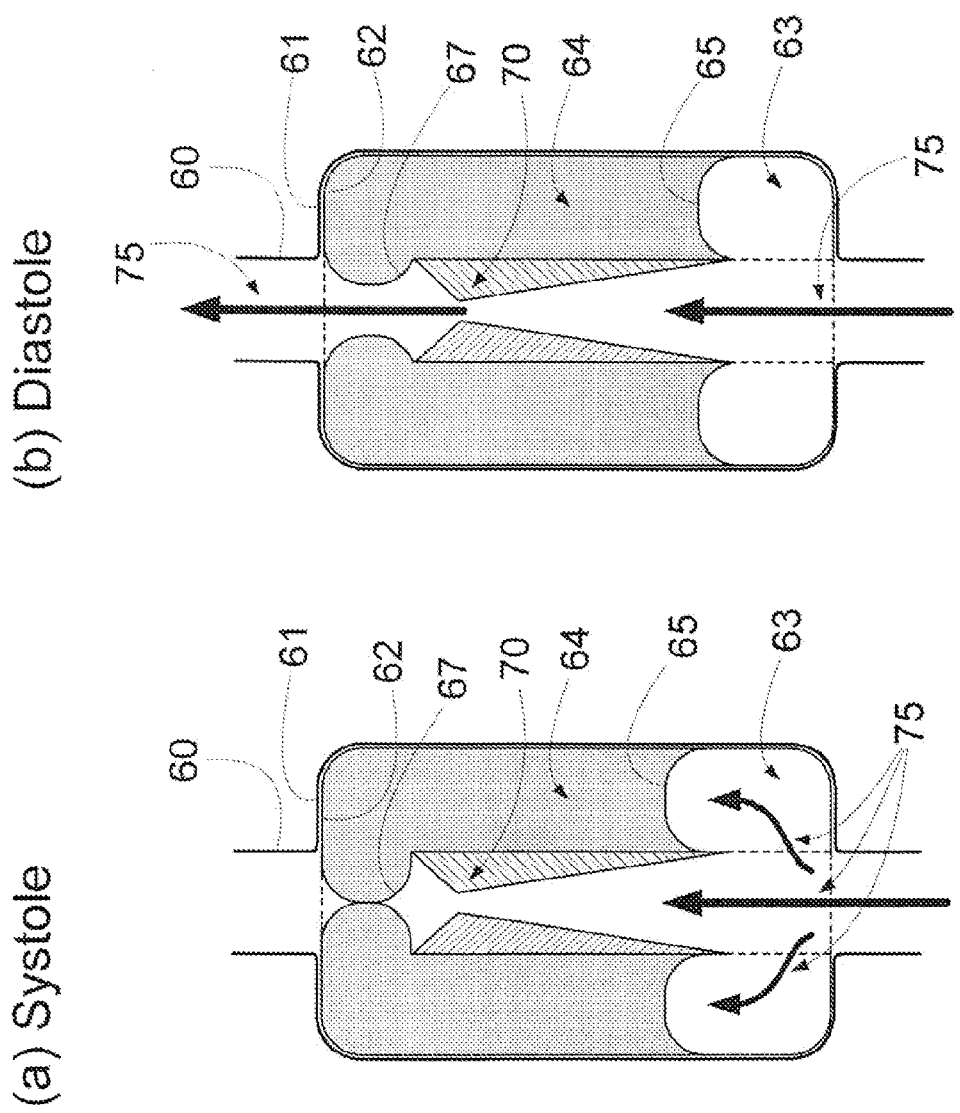
FIGS. 4(a) and 4(b) are cross-sectional views of another exemplary catheter/conduit element during systole and diastole, respectively.

FIGS. 4a and 4b illustrate another exemplary apparatus of the present invention having a catheter 60 with a chamber section 61 about the distal end of the catheter 60 A separate elongate hollow-walled conduit element 62 is provided inside the chamber section 61. The chamber 64 defining the hollow-walled conduit element 62 is filled with a selected displaceable medium exemplified by fluids, gels, gases and the like, which is sealably contained therein. The proximal end of the chamber section 62 comprises an inner-facing area formed into a concave pocket 63 and a resiliently deformable first diaphragm 65 providing a leak-proof seal for containing the displaceable medium within the hollow-walled conduit element 62. The concave pocket 63 communicates with the lumen of the catheter 15. A resiliently deformable second diaphragm 67 is provided at the distal end of the hollow-walled conduit element 62. The second diaphragm 67 encircles the lumen of the catheter 15. The inner face 70 of the hollow-walled conduit element 62 is stiffened and tapered with a larger diameter at the proximal end adjacent the concave pocket 63 and a narrower diameter at the distal end of the hollow-walled conduit element 62 adjacent the second diaphragm 67. It is optional for the thickness of the stiffened inner face 70 to be increased as the diameter of the lumen is narrowed from the proximal end to the distal end of the hollow-walled conduit element 62. The tapered inner face region 70 of the lumen may provide an artificial stenosis (i.e., a pressure gradient of about 20 to about 30 mmHg) during pulsed flow of a fluid through the hollow-walled conduit element 62.

The displaceable medium sealed within the hollow-walled conduit element 62 is controllably shiftable to alternately occlude and allow flow of oxygenated blood 75 through the catheter 60 in synchrony with a subject's cardiac cycle. During the systolic phase (FIG. 4*a*), pressurized oxygenated blood flows (shown by the arrows 75) into the pocket area 63 and pushes on the first diaphragm 65 causing it to progressively deform from its resting position into the hollow-walled conduit element 62 thereby causing displacement of the displaceable medium within the hollow wall toward the second diaphragm 67. This displacement of displaceable medium within the hollow wall causes the second diaphragm 67 to deform from its resting position outward into the lumen of the catheter 60, thereby increasingly occluding the flow of oxygenated blood 75 through the catheter 60. During the diastolic phase (FIG. 4*b*), pressurized flow of oxygenated blood 75 through the catheter 60 decreases thus allowing oxygenated blood 75 to flow out of the pocket area 63 thereby reducing and releasing pressure on the first diaphragm 65 allowing it to return to its resting position. This in turn allows the displaceable medium sealed within the hollow wall of the conduit element 60 to reduce and release pressure on the second diaphragm 67 allowing it to return to its resting position resulting in removal of the occlusion of the lumen of the catheter 15.

The conduit element and occluding conduit are composed of a suitable compliant material known to those skilled in these arts. The catheter comprises a flexible material to allow for manipulation and placement within the coronary sinus. A distal end region (that placed within the coronary sinus) may be significantly less compliant than the remainder of the catheter, so as to provide support to the conduit element when the lumen is pressurized with the oxygenated blood. In an alternate embodiment, the catheter may comprise a suitable flexible, compliant material throughout, with a stiffener applied to the distal end region to provide suitable support to the conduit element. Such a stiffener may be a metal, plastic or polymer coil of substantially non-compliant material to prevent distortion of the shape of the catheter within the coronary sinus, but allow for the flexibility necessary to maneuver the catheter to the coronary sinus.

The hollow-walled conduit element can comprise any resilient material suitable for installation into mammalian organs and tissues.

The catheter may be inserted intraoperatively (e.g. during surgery when the thoracic cavity is accessible) using a stylet or retractable cannula; alternately, the catheter may be positioned percutaneously using a guidewire extending through the catheter.

It is within the scope of the present invention for some exemplary embodiments of the apparatus to be configured for perfusion of a patient's organs and tissues with oxygenated blood routed to the apparatus from a suitable artery within the patient's body. Furthermore, it is within the scope of the present invention to supplement the patient's arterial supply of oxygenated blood with suitable blood substitute. A blood substitute is a medium that may be used to carry dissolved oxygen and/or other gases in the cardiovascular system; examples of blood substitutes include hemoglobin glutamers (e.g., Hemopure®, Oxyglobin®), perfluorocarbon emulsions (e.g. Oxygent), hemoglobin polymers (e.g. PolyHeme), perfluorodecalin (e.g. Fluosol-DA-20) and the like. (Hemopure and Oxyglobin are registered trademarks of BioPure Corporation, Boston Mass.).

One or more currently preferred embodiments of the invention have been described by way of example. The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

What is claimed is:

1. An apparatus for retroperfusion of an organ or tissue, the apparatus comprising;
    a catheter for conveying a flow of a fluid medium, the catheter having a proximal end for engaging a supply of the fluid medium and a distal end for installation into a coronary sinus within a patient's body;
    an elongate expandable chamber installed about the distal end of the catheter, the chamber comprising a sealed hollow-walled conduit defining a lumen for housing the catheter therethrough, wherein the lumen is provided with a first deformable resilient section at a resting position approximate a proximal end of the elongate expandable chamber and a second deformable resilient section at a resting position approximate a distal end of the elongate expandable chamber; and
    a displaceable medium contained within the sealed hollow-walled conduit, whereby application of a pressure to a fluid flow through the catheter at the proximal end of the elongate expandable chamber will cause the first deformable resilient section to form an inward-extending pocket, thereby displacing the displaceable medium toward the distal end of the elongate expandable chamber, thereby causing the second deformable resilient section to deform out-ward thereby occluding the distal end of the catheter; and
    release of the pressure to fluid flow through the catheter at the proximal end of the elongate expandable chamber will cause the first deformable resilient section to return to its resting position, thereby displacing the displaceable medium toward the proximal end of the elongate expandable chamber, thereby causing the second deformable resilient section to return to its resting position.

2. The apparatus of claim 1, additionally configured to cooperate with a pressure monitoring device.

3. The apparatus of claim 2, wherein the pressure monitoring device is communicable with a flow of fluid medium within the catheter.

4. The apparatus of claim 1, wherein the proximal end of the catheter is configured to engage a supply of arterial blood from a subject wherein the apparatus is installed.

5. The apparatus of claim 1, wherein the proximal end of the catheter is configured to engage a packaged supply of an oxygenated fluid medium.

6. The apparatus of claim 1, wherein the fluid medium comprises blood and/or a blood substitute.

7. The apparatus of claim 1, additionally comprising a conduit sealably interconnected with the catheter at a position proximal to the elongate expandable chamber, wherein the conduit is configured for conveying a fluid composition to the catheter for commingling therewith the fluid medium.

8. The apparatus of claim 1, wherein a section of the lumen interposed the first deformable resilient section and the second deformable resilient section, is stiffened with a stiffening material.

9. An apparatus for retroperfusion of an organ or tissue, the apparatus comprising;
   a catheter for conveying a flow of a fluid medium, the catheter having a proximal end for engaging a supply of the fluid medium and a distal end for installation into a coronary sinus within a patient's body;
   a first elongate expandable chamber installed about the distal end of the catheter, the first chamber comprising a first sealed hollow-walled conduit defining a first lumen for housing the catheter therethrough;
   a second elongate chamber installed about the catheter at a location proximate to the first elongate expandable chamber, the second elongate chamber comprising a second sealed hollow-walled conduit defining a second lumen for housing the catheter therethrough, wherein the second lumen is provided with a first deformable resilient section at a resting position approximate a proximal end of the second elongate expandable chamber and a second deformable resilient section at a resting position approximate a distal end of second elongate expandable chamber; and
   a displaceable medium contained within the second sealed hollow-walled conduit, whereby application of a pressure to a fluid flow through the catheter at the proximal end of the second elongate expandable chamber will cause the first deformable resilient section to form an inward-extending pocket, thereby displacing the displaceable medium toward the distal end of the second elongate expandable chamber, thereby causing the second deformable resilient section to deform out-ward thereby occluding the catheter; and
   release of the pressure to fluid flow through the catheter at the proximal end of the second elongate expandable chamber will cause the first deformable resilient section to return to its resting position, thereby displacing the displaceable medium toward the proximal end of the second elongate expandable chamber, thereby causing the second deformable resilient section to return to its resting position.

10. The apparatus of claim 9, additionally configured to cooperate with a pressure monitoring device.

11. The apparatus of claim 10, wherein the pressure monitoring device is communicable with a flow of fluid medium within the catheter.

12. The apparatus of claim 9, wherein the proximal end of the catheter is configured to engage a supply of arterial blood from a subject wherein the apparatus is installed.

13. The apparatus of claim 9, wherein the proximal end of the catheter is configured to engage a packaged supply of an oxygenated fluid medium.

14. The apparatus of claim 9, additionally comprising a conduit sealably interconnected with the catheter at a position proximal to the elongate expandable chamber, wherein the conduit is configured for conveying a fluid composition to the catheter for commingling therewith the fluid medium.

15. The apparatus of claim 9, wherein a section of the lumen interposed the first deformable resilient section and the second deformable resilient section, is stiffened with a stiffening material.

* * * * *